United States Patent [19]

Iwasaki et al.

[11] Patent Number: 4,840,942

[45] Date of Patent: Jun. 20, 1989

[54] EMULSIFYING DISPERSANT AND BIOCIDAL COMPOSITION CONTAINING SAME

[75] Inventors: Tetsuji Iwasaki; Yoshio Fukui, both of Wakayama, Japan

[73] Assignee: Kao Corporation, Tokyo, Japan

[21] Appl. No.: 656,835

[22] Filed: Oct. 2, 1984

[30] Foreign Application Priority Data

Oct. 14, 1983 [JP] Japan ................................ 58-192168

[51] Int. Cl.$^4$ ............................................ A01N 57/00
[52] U.S. Cl. .................................... 514/120; 514/122; 514/132; 514/136; 514/941
[58] Field of Search 514/941, 136, 122, 120; 514/132; 252/356, DIG. 1

[56] References Cited

U.S. PATENT DOCUMENTS

| | | | |
|---|---|---|---|
| Re. 24,184 | 7/1956 | Sanders et al. | 514/941 |
| 2,577,503 | 12/1951 | Baird et al. | 252/DIG. 1 |
| 2,996,426 | 8/1961 | Galloway | 514/136 |
| 3,071,550 | 1/1963 | Altscher et al. | 514/941 |
| 3,506,588 | 4/1970 | Selz | 514/941 |
| 3,726,807 | 4/1973 | Johnson et al. | 252/DIG. 1 |
| 3,873,689 | 3/1975 | Frensch et al. | 514/941 |
| 3,894,149 | 7/1975 | Mast | 514/941 |

*Primary Examiner*—Douglas W. Robinson
*Assistant Examiner*—J. Kilcoyne
*Attorney, Agent, or Firm*—Flynn, Thiel, Boutell & Tanis

[57] ABSTRACT

An emulsifying dispersant is disclosed which is a nonionic surface active agent substantially free of a terminal primary hydroxyl group, obtained by esterifying or etherifying a terminal hydroxyl group of an alkylene oxide adduct of a hydroxyl compound or an alkylene oxide adduct of a carboxyl compound. This emulsifying dispersant is remarkably effective for preventing decomposition of a biocidal agent and for emulsifying the biocidal agent. A biocidal preparation formed using this emulsifying dispersant has good storage stability and good emulsion stability.

15 Claims, No Drawings

EMULSIFYING DISPERSANT AND BIOCIDAL COMPOSITION CONTAINING SAME

The present invention relates to an emulsifying dispersant. More particularly, the present invention relates to an emulsifying dispersant that makes it possible to incorporate a chemically unstable biocidal agent in a stable biocidal preparation.

Biocidal agents are formed into various preparations, such as emulsions, wettable powders, flowable agents, granules and dusts, and they are marketed in the form of such preparations. Among these preparations, emulsions and wettable powders are most popular, and various measures have been taken in the prior art for obtaining stable preparations of these types. The decomposition of a biocidal agent during storage is a fatal defect for a commercial preparation, and entails a risk of phytotoxicity caused by substances produced by such decomposition. As factors which cause the decomposition of a biocidal agent during storage of a preparation containing the agent, heat, light (ultraviolet radiation), water heavy metals, emulsifiers and dispersants are considered most important. The effects of external factors, such as light and heat, can be eliminated by using a specially designed packaging vessel or by similar measures which protect the biocidal composition from the external factor. The problem of hydrolysis caused by water can be solved by employing an organic solvent-based emulsion other than a flowable composition.

When an agricultural biocidal composition is actually used, it is diluted with water and then sprayed onto the plants. Therefore, it is necessary to incorporate into the composition an emulsifier capable of emulsifying a water-insoluble organic solvent and a water-insoluble agricultural biocidal agent. However, from the results of our research, we have found that one type of decomposition of agricultural biocides, which we consider is due to the presence of a primary hydroxyl group in the emulsifier molecules, cannot be avoided when known emulsifiers for agricultural biocides having primary hydroxyl groups are used. Moreover, even in the case of wettable powders containing an inorganic carrier, decomposition due to (a) water contained in the inorganic substance, (b) surface hydroxyl groups, (c) heavy metals and (d) dispersants cannot be avoided. At present, this problem can be solved only with difficulty by modifying the surface of the inorganic carrier or by adding a decomposition-preventing agent, but no commercially satisfactory results have yet been obtained.

We have studied the problem of minimizing or preventing decomposition of agricultural chemicals, particularly pesticides, caused by emulsifiers or dispersants. We found that the decomposition is mainly due to the presence of a hydroxyl group in the molecular skeleton of the surface active agent that is employed as an emulsifier or dispersant. Accordingly, we continued our research with a view to developing a surface active agent free of this defect, and as a result, we have now completed the present invention.

More specifically, in accordance with the present invention, there is provided an emulsifying dispersant (surfactant) for forming a stable preparation of a biocidal agent, which surfactant comprises a nonionic surface active agent substantially free of terminal primary hydroxyl groups. The surfactant of this invention is obtained by esterifying or etherifying a terminal hydroxyl group of an alkylene oxide adduct of a hydroxyl compound or an alkylene oxide adduct of a carboxyl compound. The hydroxyl and carboxyl compounds according to this invention are preferably compounds having carboxylic or hydroxyl-substituted hydrocarbon groups. The emulsifying dispersant of the present invention not only prevents decomposition of the biocidal agent, but also has excellent emulsifying and dispersing effects.

The present invention also provides a biocidal composition which is emulsifiable in water. The biocidal composition according to the present invention contains an effective amount of a water-insoluble biocide, an amount of an organic solvent effective to dissolve the biocide, and an emulsifier which comprises the nonionic surface active agent of the invention described above. The emulsifier is used in an amount effective to emulsify the organic solvent containing the biocide dissolved therein in water.

The nonionic surfactant used in the emulsifying dispersant of the present invention cannot readily be expressed using a generic chemical formula because it includes nonionic surfactants of complex formulas made from polyhydric alcohols, such as polyoxyethylene glycerol trioleate, polyoxyethylene sorbitol hexaoleate, and similar compounds. However, the simpler nonionic surfactants used in the present invention can be expressed by the following general formula:

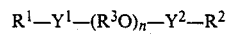
$$R^1-Y^1-(R^3O)_n-Y^2-R^2$$

wherein $R^1$ and $R^2$ are each a saturated or ethylenically unsaturated hydrocarbon group, with the proviso that at least one of $R^1$ and $R^2$ has at least 8 carbon atoms, $Y^1$ is —COO— or —O—, $Y^2$ is —OC— or represents a direct valence bond between $-(R^3O)_n-$ and $-R^2$, $R^3$ is $C_2$-$C_4$ alkylene, and n is an integer of from 1 to 100.

More specifically, the nonionic surfactants have one of the following formulas:

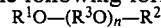
$$R^1O-(R^3O)_n-R^2$$

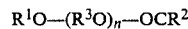
$$R^1O-(R^3O)_n-OCR^2$$

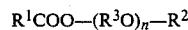
$$R^1COO-(R^3O)_n-R^2$$

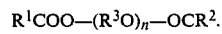
$$R^1COO-(R^3O)_n-OCR^2.$$

The biocidal composition of the present invention preferably contains 10 to 90 wt.% of the water-insoluble biocide, 15 to 50 wt.% of the organic solvent, and 1 to 50 wt.% of the emulsifier. The organic solvent is preferably an aromatic hydrocarbon. particularly xylene. The biocide is any water-insoluble insecticide, herbicide or other pesticide. Mose preferably, the biocidal composition contains 10 to 60 wt.% of the biocide, 20 to 50 wt.% of the organic solvent, and 5 to 25 wt.% of the emulsifier.

As the hydroxyl compound used for preparing the surface active agent of the present invention, there can be used natural and synthetic aliphatic alcohols such as methyl alcohol, ethyl alcohol, propyl alcohol, butyl alcohol, octyl alcohol, 2-ethylhexyl alcohol, lauryl alcohol, tridecyl alcohol, cetyl alcohol, stearyl alcohol and oleyl alcohol, polyhydric alcohols such a glycerol, polyglycerol, sorbitol, sucrose, pentaerythritol and trimethylolpropane, alkylphenols such as octylphenol and nonylphenol, and aromatic-substituted phenols such as phenylphenol, tribenzylphenol and styrenated phenol.

As the carboxyl compound used for preparing the surface active agent of this invention, carboxylic acids having 2 to 22 carbon atoms can be used, such as acetic acid, propionic acid, caprylic acid, capric acid, 2-ethylhexanoic acid, lauric acid, myristic acid, palmitic acid, stearic acid and oleic acid.

The alkylene oxide adduct can be prepared from a hydroxyl or carboxyl compound as described above according to known methods, for example, a method comprising reacting a hydroxyl or carboxyl compound, with an alkylene oxide compound in the presence of an alkali or acid catalyst.

As the alkylene oxide compound, there can be used ethylene oxide, propylene oxide and butylene oxide. Ethylene oxide is especially preferred. If an alkylene oxide mixture is used, the content of ethylene oxide is preferably at least 30 mole %. The number of moles of added alkylene oxide is 1 to 100, preferably 5 to 50 moles, per 1 mole of the hydroxyl or carboxyl compound to be reacted therewith.

Esterification or etherification of the alkylene oxide adduct can be performed according to known methods. For example, an esterification method may be used which comprises dehydrating and esterifying the alkylene oxide adduct with a fatty acid in the presence of an acid or alkali catalyst. An etherification method comprising dehydrohalogenating the alkylene oxide adduct with an alkyl halide in the presence of caustic alkali can also be used.

A fatty acid halide or fatty acid anhydride can be used as the esterifying agent instead of the abovementioned fatty acid. An esterifying agent having a saturated or unsaturated hydrocarbon group of 1 to 21 carbona toms, such as capric acid, lauric acid, stearic acid or oleic acid, is preferred.

An alkyl halide having a saturated or unsaturated hydrocarbon group of 1 to 22 carbon atoms is preferred as the etherifying agent. For example, methyl chloride, ethyl chloride, propyl chloride, octyl bromide, lauryl chloride and stearyl chloride can be used.

The compound obtained by esterification or etherification is a nonionic surface active agent substantially free of a terminal hydroxyl group. It is essential that at least one of either (1) the hydrocarbon group of the starting hydroxyl or carboxyl compound or (2) the hydrocarbon group of the esterifying or etherifying agent should have at least 8 carbon atoms.

As specific examples of the nonionic surface active agents of the present invention, there can be mentioned polyoxyethylene(15) lauryl methyl ether, polyoxyethylene(20) stearyl methyl ether, polyoxyethylene(20) methyl ether oleate, polyoxyethylene(15) methyl ether laurate, polyoxyethylene(15) nonylphenyl methyl ether, polyoxyethylene(30) nonylphenyl octanoate, polyoxyethylene(30) styrylphenyl methyl ether, polyoxyethylene(30) sorbitol hexaoleate, polyoxyethylene styrenated phenyl lauryl ether, polyoxyethylene glycerol trioleate, polyoxyethylene tribenzylphenyl ethyl ether, polyoxypropylene polyoxyethylene laurylphenyl methyl ether, polyoxyethylene pentaerythritol tetra-2-ethyl hexyl ether.

Because the nonionic surface active agent of the present invention has no primary hydroxyl group, it does not decompose biocidal agents. Furthermore, because it has an excellent surface activating property, it forms a stable emulsion or dispersion of a biocidal agent.

It is preferred that the emulsifying dispersant of the present invention contain an anionic surface active agent in addition to the above-mentioned specific nonionic surfactant. As such anionic surface active agents, there can be used calcium alkylbenzenesulfonate and triethanolamine alkylbenzenesulfonate. In preferred embodiments of the invention, the emulsifier consists essentially of a mixture of 55 to 80 wt.% of the nonionic surface active agent and 45 to 20 wt.% of the anionic surface active agent.

The present invention will now be described in detail with reference to Synthesis Examples, Examples and Comparative Examples.

An emulsifier composition was first prepared according to an emulsifier formulation example, and then a preparation according to each example or comparative example was formed by emulsifying a solvent and an agricultural biocide with the emulsifier composition. Then, the stability of each resulting preparation was tested.

SYNTHESIS EXAMPLE

In this Synthesis Example, polyoxyethylene(20) methyl ether oleate was synthesized.

An autoclave (formed of SUS) having a capacity of 3.0 l and provided with an electromagnetic stirrer was charged with 64 g (2.0 moles) of methanol and 2.2 g of caustic potash. The inner atmosphere of the autoclave was purged with nitrogen and the charge was heated to 90 ±5° C. Then, 1762 g of ethylene oxide was fed under pressure at 90 to 130° C. over a period of 4 to 5 hours so that the reaction pressure did not exceed 3.5 kg/cm$^2$G, whereby the reaction was completed.

The reaction product was neutralized with acetic acid to obtain POE(20) methyl ether having a hydroxyl value of 62 mg KOH/g and a color of APHA 20. Then, a 2-liter capacity 4-neck flask provided with a thermometer, a stirrer, a water removing tube and a nitrogen inlet tube was charged with 932 g (1.03 mole) of the thus-obtained POE(20) methyl ether, 274 g (1.0 mole) of oleic acid and 2.4 g of 85 % H$_3$PO$_4$, the mixture was heated at 215°±5° C., and reaction was carried out at this temperature for about 7 to 8 hours to obtain a liquid reaction product having a color of APHA 150 to 200, an acid value of 6 mg KOH/g, a saponification value of 48 mg KOH/g and a hydroxyl value of 9 mg KOH/g.

The following emulsifier formulations were then prepared, using the thus-prepared polyoxyethylene(20) methyl ether oleate and other surfactants, as follows:

| Emulsifier Formulation Example 1 | |
| --- | --- |
| Polyoxyethylene(20) methyl ether oleate | 30% by weight |
| Polyoxyethylene(13) nonylphenyl methyl ether | 40% by weight |
| Calcium alkylbenzenesulfonate | 30% by weight |
| Emulsifier Formulation Example 2 | |
| Polyoxyethylene(15) styrenated phenyl lauryl ether | 50% by weight |
| Polyoxyethylene(30) glycerol trioleate | 25% by weight |
| Calcium alkylbenzenesulfonate | 25% by weight |
| Emulsifier Formulation Example 3 | |
| Polyoxyethylene(20) tribenzylphenyl ethyl ether | 30% by weight |
| Polyoxyethylene(50) sorbitol hexaoleate | 25% by weight |
| Triethanolamine alkylbenzenesulfonate | 45% by weight |
| Emulsifier Formulation Example 4 | |
| Polyoxypropylene(10) polyoxyethylene(20) laurylphenyl methyl ether | 40% by weight |
| Polyoxyethylene(40) pentaerythritol tetra-2-ethylhexyl ether | 40% by weight |
| Sorbitan oleate | 20% by weight |
| Comparative Emulsifier Formulation Example 1 | |
| Polyoxyethylene(20) mono-oleate | 30% by weight |
| Polyoxyethylene(13) nonylphenol ether | 30% by weight |
| Calcium alkylbenzenesulfonate | 40% by weight |

-continued

| Comparative Emulsifier Formulation Example 2 | |
|---|---|
| Polyoxyethylene(15) styrenated phenol ether | 60% by weight |
| Calcium alkylbenzenesulfonate | 40% by weight |
| Comparative Emulsifier Formulation Example 3 | |
| Polyoxyethylene(20) tribenzylphenol ether | 55% by weight |
| Triethanolamine alkylbenzenesulfonate | 45% by weight |
| Comparative Emulsifier Formulation Example 4 | |
| Polyoxypropylene(10) polyoxyethylene(20) laurylphenyl ether | 40% by weight |
| Polyoxyethylene(40) pentaerithritol | 40% by weight |
| Sorbitan oleate | 20% by weight |
| Example 1 | |
| Malathion | 55% by weight (A.I.* 51.8) |
| Xylene | 35% by weight |
| Emulsifier Formulation Example 1 | 10% by weight |
| Comparative Example 1 | |
| Malathion | 55% by weight (A.I. 51.8) |
| Xylene | 35% by weight |
| Comparative Emulsifier Formulation Example 1 | 10% by weight |
| Example 2 | |
| Sumithion | 55% by weight (A.I. 52.6) |
| Xylene | 35% by weight |
| Emulsifier Formulation Example 2 | 10% by weight |
| Comparative Example 2 | |
| Sumithion | 55% by weight (A.I. 52.6) |
| Xylene | 35% by weight |
| Comparative Emulsifier Formulation Example 2 | 10% by weight |
| Example 3 | |
| DDVP (dichlorvos) | 55% by weight (A.I. 52.7) |
| Xylene | 35% by weight |
| Emulsifier Formulation Example 3 | 10% by weight |
| Comparative Example 3 | |
| DDVP | 55% by weight (A.I. 52.7) |
| Xylene | 35% by weight |
| Comparative Emulsifier Formulation Example 3 | 10% by weight |
| Example 4 | |
| Phenthoate (also known as Papthion) | 55% by weight (A.I. 51.4) |
| Xylene | 35% by weight |
| Comparative Emulsifier Formulation Example 4 | 10% by weight |

*A.I. means the active ingredient content.

Test

The storage stability and emulsion stability of each of the preparations obtained in Examples 1 through 4 and Comparative Examples 1 through 4 were examined according to the methods described below. The obtained results are given in Table 1.

(1) Storage Stability (retention of active ingredient)

Each preparation was stored at 50° C. for 3 months, and the content of the active ingredient was determined by gas chromatography according to the Japanese officially determined method for agricultural chemicals.

(2) Emulsion Stability

Each preparation was diluted by 20 times with standard water of 3 HD or 10 HD, and, after 2 hours, the emulsion stability was evaluated using the following criterion:
A: creaming or sedimentation was not observed at all
AB: less than 1 mm creaming and sedimentation
B: 1 to less than 3 mm creaming and sedimentation
C: 3 to less than 5 mm creaming and sedimentation

TABLE 1

| | Active Ingredient Amount (%) | | | | Emulsion Stability | |
|---|---|---|---|---|---|---|
| | 0 day (at start) | 30 days | 60 days | 90 days | at time of formation | 90 days |
| Example 1 | 51.8 | 51.8 | 51.7 | 51.7 | A | A |
| Comparative Example 1 | 51.8 | 50.0 | 46.5 | 40.0 | A | B |
| Example 2 | 52.6 | 52.6 | 52.6 | 52.6 | A | A |
| Comparative Example 2 | 52.6 | 50.8 | 49.7 | 46.8 | A | AB |
| Example 3 | 52.7 | 52.7 | 51.9 | 51.0 | A | A |
| Comparative Example 3 | 52.7 | 50.1 | 47.1 | 42.1 | A | AB-A |
| Example 4 | 51.4 | 51.4 | 51.4 | 51.0 | A | A |
| Comparative Example 3 | 51.4 | 50.0 | 49.4 | 41.1 | A | C |

As is apparent from the results shown in Table 1, when the emulsifying dispersant of the present invention is used, the storage stability of the biocidal agents and the emulsion stability can be maintained at the same high levels as at the time of formation of each preparation, even after storage for up to 90 days.

What is claimed is:

1. An agricultural biocidal composition which is emulsifiable in water, consisting essentially of: from 10 to 90% by weight of a water-insoluble agricultural biocide selected from the group consisting of pesticides and herbicides, from 15 to 50% by weight of a water-insoluble organic solvent in which said biocide is dissolved and from 1 to 50% by weight of an emulsifier comprising a nonionic surfactant of the formula:

$$R^1-Y^1-(R^3O)_n-Y^2-R^2$$

wherein $R^1$ and $R^2$ are each a saturated or ethylenically unsaturated hydrocarbon group, with the proviso that at least one of $R^1$ and $R^2$ has at least 8 carbon atoms, $Y^1$ is -COO- or —O—, $Y^2$ is —OC— or represents a direct valence bond between $(R^3O)_n$ and $R^2$, $R^3$ is $C_2$-$C_4$ alkylene, and n is an integer of from 1 to 100.

2. A composition as claimed in claim 1, wherein said composition consists essentially of 10-60 wt.% of said biocide, 20-50 wt.% of said organic solvent, and 5 to 25 wt.% of said emulsifier.

3. A composition as claimed in claim 1, wherein said biocide is selected from the group consisting of malathion, sumithion, dichlorvos and papthion.

4. A composition as claimed in claim 1, wherein said organic solvent is an aromatic hydrocarbon.

5. A composition as claimed in claim 4, wherein said organic solvent is xylene.

6. A composition as claimed in claim 1, wherein said nonionic surfactant has the formula:
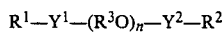
$R^1O-(R^3O)_n-R^2$.

7. A composition as claimed in claim 1, wherein said nonionic surfactant has the formula:

$R^1O-(R^3O)_n-OCR^2$.

8. A composition as claimed in claim 1, wherein said nonionic surfactant has the formula:

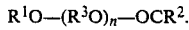
$R^1COO-(R^3O)_n-R^2$.

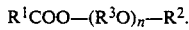

9. A composition as claimed in claim 1, wherein said nonionic surfactant has the formula:
$R^1COO-(R^3O)_n-OCR^2$.

10. A composition as claimed in claim 1 in which said emulsifier consists essentially of from 55 to 80% by weight of said nonionic surfactant and from 20 to 45% by weight of an anionic surfactant.

11. A biocidal composition as claimed in claim 10, wherein said anionic surfactant is selected from the group consisting of: calcium alkylbenzenesulfonate and triethanolamine alkylbenzenesulfonate.

12. A composition as claimed in claim 1 in which said biocide is malathion, said solvent is xylene and said emulsifier consists of 30% by weight of polyoxyethylene (20) methyl ether oleate, 40% by weight of polyoxyethylene (13) nonylphenyl methyl ether and 30% by weight of calcium alkylbenzenesulfonate.

13. A composition as claimed in claim 1 in which said biocide is sumithion, said solvent is xylene and said emulsifier consists of 50 % by weight of polyoxyethylene (15) styrenated phenyl lauryl ether, 25% by weight of polyoxyethylene (30) glycerol trioleate and 25% by weight of calcium alkylbenzenesulfonate.

14. A composition as claimed in claim 1 in which said biocide is dichlorvos, said solvent is xylene and said emulsifier consists of 30% by weight of polyoxyethylene (20) tribenzylphenylethyl ether, 25% by weight of polyoxyethylene (50) sorbitol hexaoleate and 45% by weight of triethanolamine alkylbenzenesulfonate.

15. A composition as claimed in claim 1 in which said biocide is phenthoate, said solvent is xylene and said emulsifier consists of 40% by weight of polyoxypropylene (10) poloxyethylene (20) laurylphenyl methyl ether, 40% by weight of polyoxyethylene (40) pentaerythritol tetra-2-ethyl hexyl ether and 20% by weight of sorbitan oleate.

* * * * *